(12) United States Patent
Eidenschink

(10) Patent No.: US 7,731,741 B2
(45) Date of Patent: Jun. 8, 2010

(54) INFLATABLE BIFURCATION STENT

(75) Inventor: Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 466 days.

(21) Appl. No.: 11/221,558

(22) Filed: Sep. 8, 2005

(65) Prior Publication Data
US 2007/0055356 A1 Mar. 8, 2007

(51) Int. Cl.
A61F 2/06 (2006.01)
(52) U.S. Cl. ............. 623/1.11; 623/1.25; 623/1.35
(58) Field of Classification Search .......... 623/1.1, 623/1.11, 1.25, 1.2, 1.35, 136
See application file for complete search history.

(56) References Cited

U.S. PATENT DOCUMENTS

| | | | |
|---|---|---|---|
| 4,309,994 A | 1/1982 | Grunwald | 128/214 R |
| 4,769,005 A | 9/1988 | Ginsburg et al. | 604/53 |
| 4,774,949 A | 10/1988 | Fogarty | 128/348.1 |
| 4,896,670 A | 1/1990 | Crittenden | 606/194 |
| 4,905,667 A | 3/1990 | Foerster et al. | 128/4 |
| 4,994,071 A | 2/1991 | MacGregor | 606/194 |
| 5,342,387 A | 8/1994 | Summers | 606/198 |
| 5,387,235 A | 2/1995 | Chuter | 623/1 |
| 5,456,712 A | 10/1995 | Maginot | 623/1 |
| 5,476,471 A | 12/1995 | Shifrin et al. | 606/151 |
| 5,487,730 A | 1/1996 | Marcadis et al. | 604/96 |
| 5,591,228 A | 1/1997 | Edoga | 623/1 |
| 5,596,020 A | 1/1997 | Morris et al. | 514/646 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |

(Continued)

FOREIGN PATENT DOCUMENTS

CA 2220864 7/1999

(Continued)

OTHER PUBLICATIONS

U.S. Appl. No. 09/325,996, filed Jun. 4, 1999, Vardi et al.

(Continued)

Primary Examiner—Todd E Manahan
Assistant Examiner—Diane Yabut
(74) Attorney, Agent, or Firm—Vidas, Arrett & Steinkraus, P.A.

(57) ABSTRACT

A stent may comprise a graft having a plurality of outwardly deployable petals. A petal may include an internal inflation pocket. Upon inflation, the petal may deploy outwardly and provide support to a portion of a vessel bifurcation. Inflation may be accomplished by injecting an inflation medium into the inflation pocket. In some embodiments, an inflation medium may comprise a hardening resin.

24 Claims, 6 Drawing Sheets

U.S. PATENT DOCUMENTS

| | | | |
|---|---|---|---|
| 5,707,348 A | 1/1998 | Krogh | 602/41 |
| 5,709,713 A | 1/1998 | Evans et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,851,464 A | 12/1998 | Davila et al. | 264/103 |
| 5,868,777 A | 2/1999 | Lam | 606/194 |
| 5,871,537 A | 2/1999 | Holman et al. | 623/1 |
| 5,893,887 A | 4/1999 | Jayaraman | 623/1 |
| 5,922,021 A | 7/1999 | Jang | 623/1 |
| 5,961,548 A | 10/1999 | Shmulewitz | 623/1 |
| 5,968,089 A * | 10/1999 | Krajicek | 623/1.15 |
| 5,972,017 A | 10/1999 | Berg et al. | 606/198 |
| 6,009,951 A * | 1/2000 | Coronado et al. | 166/387 |
| 6,013,054 A | 1/2000 | Jiun Yan | 604/96 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,434 A | 3/2000 | Borghi | 623/1 |
| 6,033,435 A | 3/2000 | Penn et al. | 623/1 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,086,611 A | 7/2000 | Duffy et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,123,721 A | 9/2000 | Jang | 623/1 |
| 6,129,738 A | 10/2000 | Lashinski et al. | 606/194 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,203,568 B1 | 3/2001 | Lombardi et al. | 623/1.13 |
| 6,210,380 B1 | 4/2001 | Mauch | 604/284 |
| 6,210,429 B1 * | 4/2001 | Vardi et al. | 623/1.11 |
| 6,210,433 B1 | 4/2001 | Larre | 623/1.15 |
| 6,254,593 B1 | 7/2001 | Wilson | 606/1.11 |
| 6,258,115 B1 | 7/2001 | Dubrul | 606/200 |
| 6,258,116 B1 | 7/2001 | Hojeibane | 623/1.16 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,290,673 B1 | 9/2001 | Shanley | 604/102.02 |
| 6,293,968 B1 * | 9/2001 | Taheri | 623/1.15 |
| 6,325,826 B1 | 12/2001 | Vardi et al. | 623/1.35 |
| 6,334,867 B1 | 1/2002 | Anson | 623/1.13 |
| 6,334,870 B1 | 1/2002 | Ehr et al. | 623/1.16 |
| 6,346,089 B1 | 2/2002 | Dibie | 603/1.15 |
| 6,348,065 B1 | 2/2002 | Brown et al. | 623/1.16 |
| 6,355,060 B1 | 3/2002 | Lenker et al. | 623/1.34 |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,436,104 B2 | 8/2002 | Hojeibane | 606/108 |
| 6,436,134 B2 | 8/2002 | Richter et al. | 623/1.15 |
| 6,478,816 B1 | 11/2002 | Kveen et al. | 623/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,579,309 B1 | 6/2003 | Loos et al. | 623/1.16 |
| 6,579,312 B2 | 6/2003 | Wilson et al. | 623/1.35 |
| 6,582,394 B1 | 6/2003 | Reiss et al. | 604/96.01 |
| 6,596,020 B2 | 7/2003 | Vardi et al. | 623/1.11 |
| 6,599,316 B2 | 7/2003 | Vardi et al. | 623/1.15 |
| 6,645,242 B1 * | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Callol et al. | 623/1.15 |
| 6,776,793 B2 | 8/2004 | Brown et al. | 623/1.15 |
| 6,811,566 B1 | 11/2004 | Penn et al. | 623/1.15 |
| 6,835,203 B1 | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,699 B2 | 5/2005 | Wilson et al. | 623/1.35 |
| 6,932,837 B2 | 8/2005 | Amplatz et al. | 623/1.15 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,056,323 B2 | 6/2006 | Mareiro et al. | 606/108 |
| 7,060,091 B2 | 6/2006 | Killion et al. | 623/1.15 |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereume et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0023369 A1 | 9/2001 | Chobotov | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 | 4/2002 | Vardi et al. | 623/1.35 |
| 2002/0052648 A1 | 5/2002 | McGuckin, Jr. et al. | 623/1.35 |
| 2002/0072790 A1 | 6/2002 | McGuckin, Jr. et al. | 623/1.12 |
| 2002/0111675 A1 | 8/2002 | Wilson | 623/1.35 |
| 2002/0156516 A1 | 10/2002 | Vardi et al. | 623/1.11 |
| 2002/0156517 A1 | 10/2002 | Perouse | 623/1.11 |
| 2002/0165604 A1 | 11/2002 | Shanley | 623/1.15 |
| 2002/0173835 A1 | 11/2002 | Bourang et al. | 623/1.11 |
| 2002/0173840 A1 | 11/2002 | Brucker et al. | 623/1.16 |
| 2002/0183763 A1 | 12/2002 | Callol et al. | 606/108 |
| 2002/0193872 A1 | 12/2002 | Trout, III et al. | 623/1.34 |
| 2002/0193873 A1 | 12/2002 | Brucker et al. | 623/1.35 |
| 2003/0009209 A1 | 1/2003 | Hojeibane | 623/1.11 |
| 2003/0028233 A1 | 2/2003 | Vardi et al. | 623/1.11 |
| 2003/0050688 A1 | 3/2003 | Fischell et al. | 623/1.15 |
| 2003/0055378 A1 | 3/2003 | Wang et al. | 604/103.07 |
| 2003/0055483 A1 | 3/2003 | Gumm | 623/1.11 |
| 2003/0074047 A1 | 4/2003 | Richter | 623/1.11 |
| 2003/0093109 A1 | 5/2003 | Mauch | 606/194 |
| 2003/0097169 A1 | 5/2003 | Brucker | 623/1.11 |
| 2003/0114912 A1 | 6/2003 | Sequin et al. | 623/1.11 |

| | | | | | |
|---|---|---|---|---|---|
| 2003/0120331 A1* | 6/2003 | Chobotov et al. ......... 623/1.13 | EP | 0684022 | 2/2004 |
| 2003/0125791 A1 | 7/2003 | Sequin et al. ............. 623/1.11 | EP | 1157674 | 7/2005 |
| 2003/0125797 A1 | 7/2003 | Chobotov et al. ......... 623/1.13 | EP | 1031330 | 11/2005 |
| 2003/0125802 A1 | 7/2003 | Callol et al. ............... 623/1.35 | EP | 1070513 | 6/2006 |
| 2003/0135259 A1 | 7/2003 | Simso ....................... 623/1.12 | FR | 2678508 | 1/1993 |
| 2003/0181923 A1 | 9/2003 | Vardi ......................... 606/108 | FR | 2740346 | 10/1995 |
| 2003/0195606 A1 | 10/2003 | Davidson et al. .......... 623/1.11 | FR | 2756173 | 11/1996 |
| 2003/0216802 A1 | 11/2003 | Chobotov .................. 623/1.13 | GB | 2337002 | 5/1998 |
| 2004/0006381 A1 | 1/2004 | Sequin et al. .............. 623/1.12 | WO | 88/06026 | 8/1988 |
| 2004/0015227 A1 | 1/2004 | Vardi et al. ................. 623/1.16 | WO | 95/21592 | 8/1995 |
| 2004/0044396 A1 | 3/2004 | Clerc et al. ................. 623/1.13 | WO | 96/29955 | 10/1996 |
| 2004/0059406 A1 | 3/2004 | Cully et al. ................. 623/1.11 | WO | 96/34580 | 11/1996 |
| 2004/0088007 A1 | 5/2004 | Eidenschink ................... 607/1 | WO | 96/41592 | 12/1996 |
| 2004/0117003 A1 | 6/2004 | Ouriel et al. ............... 623/1.35 | WO | 97/07752 | 3/1997 |
| 2004/0133268 A1 | 7/2004 | Davidson et al. .......... 623/1.35 | WO | 97/15346 | 5/1997 |
| 2004/0138732 A1 | 7/2004 | Suhr et al. .................. 623/1.11 | WO | 97/16217 | 5/1997 |
| 2004/0138737 A1 | 7/2004 | Davidson et al. .......... 623/1.35 | WO | 97/26936 | 7/1997 |
| 2004/0148006 A1 | 7/2004 | Davidson et al. .......... 623/1.11 | WO | 97/41803 | 11/1997 |
| 2004/0172121 A1 | 9/2004 | Eidenschink et al. ....... 623/1.11 | WO | 97/45073 | 12/1997 |
| 2004/0186560 A1 | 9/2004 | Alt ............................. 623/1.35 | WO | 97/46174 | 12/1997 |
| 2004/0220664 A1 | 11/2004 | Chobotov .................. 623/1.13 | WO | 98/19628 | 5/1998 |
| 2004/0224047 A1 | 11/2004 | Chobotov et al. ........... 425/392 | WO | 98/36709 | 8/1998 |
| 2004/0225345 A1 | 11/2004 | Fischell et al. ............. 623/1.11 | WO | 98/37833 | 9/1998 |
| 2004/0267352 A1 | 12/2004 | Davidson et al. .......... 623/1.15 | WO | 98/47447 | 10/1998 |
| 2005/0004656 A1 | 1/2005 | Das ............................. 623/1.16 | WO | 98/48879 | 11/1998 |
| 2005/0010278 A1 | 1/2005 | Vardi et al. ................. 623/1.35 | WO | 99/03426 | 1/1999 |
| 2005/0015108 A1 | 1/2005 | Williams et al. ............ 606/194 | WO | 99/04726 | 2/1999 |
| 2005/0015135 A1 | 1/2005 | Shanley ...................... 623/1.11 | WO | 99/15103 | 4/1999 |
| 2005/0060027 A1 | 3/2005 | Khenansho et al. ........ 623/1.35 | WO | 99/15109 | 4/1999 |
| 2005/0096726 A1 | 5/2005 | Sequin et al. .............. 623/1.12 | WO | 99/24104 | 5/1999 |
| 2005/0102021 A1 | 5/2005 | Osborne ..................... 623/1.13 | WO | 99/34749 | 7/1999 |
| 2005/0102023 A1 | 5/2005 | Yadin et al. ................ 623/1.15 | WO | 99/36002 | 7/1999 |
| 2005/0119731 A1 | 6/2005 | Brucker et al. ............. 623/1.35 | WO | 99/36015 | 7/1999 |
| 2005/0125076 A1 | 6/2005 | Ginn ....................... 623/23.65 | WO | 99/44539 | 9/1999 |
| 2005/0131526 A1 | 6/2005 | Wong ......................... 623/1.15 | WO | 99/56661 | 11/1999 |
| 2005/0149161 A1 | 7/2005 | Eidenschink et al. ....... 623/1.11 | WO | 99/65419 | 12/1999 |
| 2005/0154442 A1 | 7/2005 | Eidenschink et al. ....... 623/1.11 | WO | 00/07523 | 2/2000 |
| 2005/0154444 A1 | 7/2005 | Quadri ....................... 623/1.13 | WO | 00/10489 | 3/2000 |
| 2005/0183259 A1 | 8/2005 | Eidenschink et al. ......... 29/508 | WO | 00/16719 | 3/2000 |
| 2005/0209673 A1 | 9/2005 | Shaked ...................... 623/1.11 | WO | 00/27307 | 5/2000 |
| 2005/0228483 A1 | 10/2005 | Kaplan et al. .............. 623/1.15 | WO | 00/27463 | 5/2000 |
| 2005/0228484 A1 | 10/2005 | Stephens et al. ........... 623/1.16 | WO | 00/28922 | 5/2000 |
| 2006/0036315 A1 | 2/2006 | Yadin et al. ................ 623/1.35 | WO | 01/45594 | 6/2000 |
| 2006/0041303 A1 | 2/2006 | Israel ......................... 623/1.11 | WO | 00/44307 | 8/2000 |
| 2006/0079956 A1 | 4/2006 | Eigler et al. ................ 623/1.35 | WO | 00/44309 | 8/2000 |
| 2006/0173528 A1 | 8/2006 | Feld et al. .................. 623/1.15 | WO | 00/47134 | 8/2000 |
| 2007/0073376 A1 | 3/2007 | Krolik et al. ............... 623/1.11 | WO | 00/48531 | 8/2000 |
| | | | WO | 00/49951 | 8/2000 |
| | FOREIGN PATENT DOCUMENTS | | WO | 00/51523 | 9/2000 |
| DE | 9014845 | 2/1991 | WO | 00/57813 | 10/2000 |
| DE | 29701758 | 3/1997 | WO | 00/67673 | 11/2000 |
| DE | 29701883 | 5/1997 | WO | 00/71054 | 11/2000 |
| EP | 0479730 | 10/1991 | WO | 00/71055 | 11/2000 |
| EP | 0751752 | 1/1997 | WO | 00/74595 | 12/2000 |
| EP | 0783873 | 7/1997 | WO | 01/21095 | 3/2001 |
| EP | 0804907 | 11/1997 | WO | 01/21109 | 3/2001 |
| EP | 0479557 | 7/1998 | WO | 01/21244 | 3/2001 |
| EP | 0876805 | 11/1998 | WO | 01/35715 | 5/2001 |
| EP | 0880949 | 12/1998 | WO | 01/35863 | 5/2001 |
| EP | 0891751 | 1/1999 | WO | 01/39697 | 6/2001 |
| EP | 0895759 | 2/1999 | WO | 01/39699 | 6/2001 |
| EP | 0904745 | 3/1999 | WO | 01/41677 | 6/2001 |
| EP | 0937442 | 8/1999 | WO | 01/43665 | 6/2001 |
| EP | 0347023 | 12/1999 | WO | 01/43809 | 6/2001 |
| EP | 1031328 | 8/2000 | WO | 01/45785 | 6/2001 |
| EP | 1031329 | 8/2000 | WO | 01/49342 | 7/2001 |
| EP | 0883384 | 12/2000 | WO | 01/54621 | 8/2001 |
| EP | 0862392 | 8/2001 | WO | 01/54622 | 8/2001 |
| EP | 0808140 | 12/2001 | WO | 01/58385 | 8/2001 |
| EP | 0884028 | 2/2002 | WO | 01/60284 | 8/2001 |
| EP | 1190685 | 3/2002 | WO | 01/70294 | 9/2001 |
| EP | 0897700 | 7/2002 | WO | 01/70299 | 9/2001 |
| | | | WO | 01/74273 | 10/2001 |

| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |

OTHER PUBLICATIONS

U.S. Appl. No. 09/614,472, filed Jul. 11, 2000, Davidson et al.
U.S. Appl. No. 09/663,111, filed Sep. 15, 2000, Davidson et al.
Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).
Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).
Caputo, Ronald P., "Stent Jail: A Minimum-Security Prison," *The American Journal of Cardiology*, vol. 77, pp. 1226-1230 (Jun. 1, 1996).
Colombo, M.D., Antonio, ""Kissing" Stent for Bifurcational Coronary Lesion," *Catheterization and Cardiovascular Diagnosis*, vol. 30, pp. 327-330 (Dec. 1993).
Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).
Katoh, M.D., Osamu, "New Double Wire Technique to Stent Ostial Lesions," *Catheterization and Cardiovascular Diagnosis*, vol. 40, pp. 400-402 (Apr. 1997).
Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).
Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).
Satler, M.D., Lowell F., "Bifurcation Disease: To Treat or Not to Treat," *Catheterization and Cardiovascular Interventions*, vol. 50, pp. 411-412 (2000).
U.S. Appl. No. 11/138,022, filed May 26, 2005, Gregorich.
U.S. Appl. No. 11/138,196, filed May 26, 2005, Gregorich.
U.S. Appl. No. 11/138,202, filed May 26, 2005, Gregorich.

* cited by examiner

INFLATABLE BIFURCATION STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

Referring to PRIOR ART FIG. 1, when stenting at a bifurcation where a side branch vessel 4 meets a main vessel 2, a main stent 6 is placed in the main vessel 2. A side branch stent 8 is placed in the branch vessel 4. However, in some instances and especially when the acute angle between the main vessel 2 and the side branch vessel 4 is small, when the side branch stent 8 is positioned with a portion of one end 9 abutting the main stent 6, a portion of the bifurcation 5 can be left with little support.

There remains a need for a device capable of better supporting vessel portions at bifurcations.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one embodiment the invention is directed to a stent comprising a plurality of structural struts defining a tubular body having a side branch opening and a graft covering at least a portion of the structural struts. The graft further comprises an outwardly deployable petal having an inflatable pocket. The inflatable pocket defines an inflation lumen and comprises at least one inflation port. In an expanded/deployed state, the pedal extends outwardly from the tubular body.

In another embodiment the invention is directed to a stent delivery system comprising a catheter shaft having an inflation lumen and a stent comprising a graft having an outwardly deployable petal having an inflatable pocket, wherein the inflation lumen is in fluid communication with the inflatable pocket.

In another embodiment the invention is directed to a method of stenting a bifurcated vessel comprising providing a stent comprising a graft, the graft comprising an outwardly deployable petal having an inflatable pocket; orienting the stent at a deployment location; and injecting an inflation medium into the inflatable pocket, thereby deploying the petal outwardly.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

DETAILED DESCRIPTION OF THE INVENTION

Figure 3:
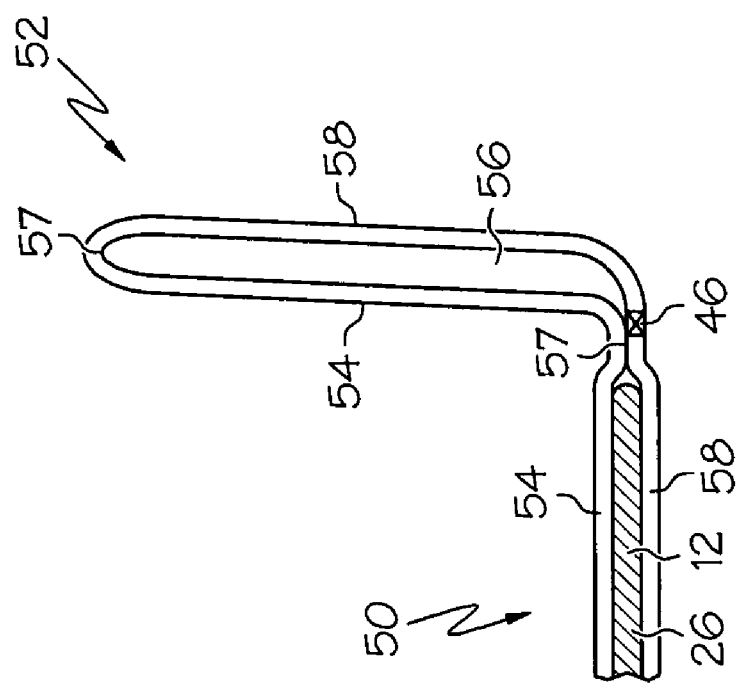
FIG. 3 shows a cross-sectional view of a portion of an inventive stent and an outwardly deployable inflatable petal.
Figure 1:
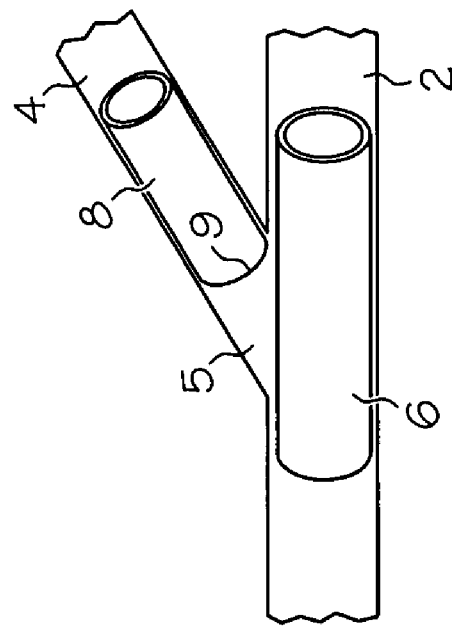
FIG. 1 shows a PRIOR ART method of stenting a bifurcation.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, or substituted for, elements depicted in another figure as desired.

Figure 2:
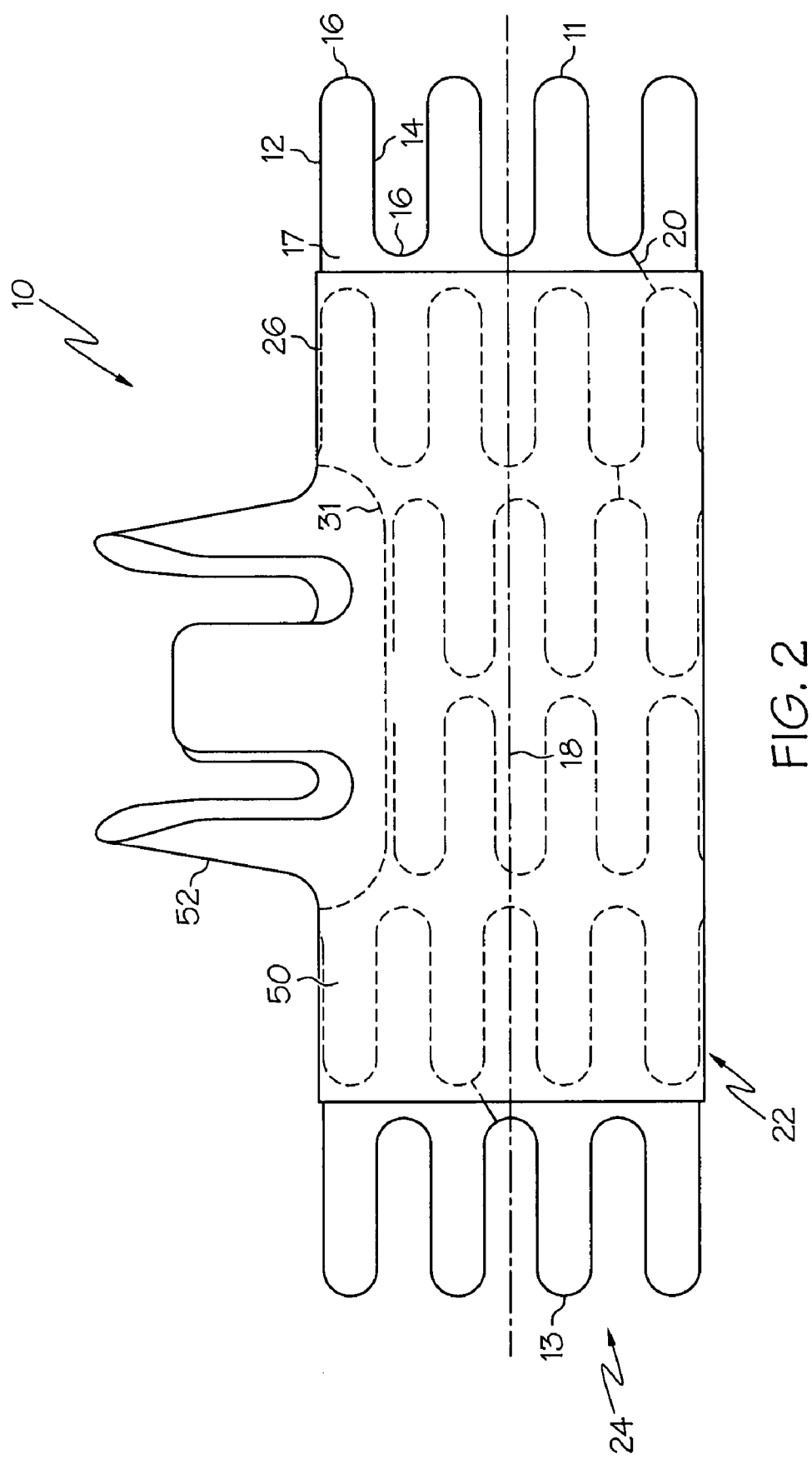
FIG. 2 shows an embodiment of an inventive stent.

FIG. 2 shows an embodiment of a stent 10 comprising a cover or graft 50 having petals 52 which may be inflatable and may fold outwardly upon inflation. The stent 10 may have an unexpanded state of a first diameter which may comprise a crimped delivery configuration. The stent 10 may be expandable from the unexpanded state to an expanded state of a second or larger diameter. In the expanded state, the petals 52 may be outwardly deployed, wherein the petals 52 extend outward from the stent body. An expanded state wherein the petals 52 are outwardly deployed may also be described as a deployed state.

The stent 10 may comprise a substantially tubular body 22 having a proximal end 11 and a distal end 13. The body 22 may have a central longitudinal axis 18 and may further define a lumen 24 extending therethrough. The body 22 may comprise a plurality of structural struts 26, which may comprise a plurality of serpentine bands 12 which may have any suitable shape, and in some embodiments may comprise a plurality of band struts 14 connected by turns 16. Adjacent serpentine bands 12 may be connected by connectors 20. The interconnected stent structural struts 26, such as band struts 14, turns 16 and connectors 20, may define a stent wall portion and may further define a plurality of cells 17. Each cell 17 may comprise an aperture or void in the stent wall portion, although some cells 17 may be covered by the graft 50.

A plurality of adjacent structural struts 26 may generally define a side branch opening 31, which may comprise a cell 17 that may be shaped differently than other cells 17 of the stent 10. The side branch opening 31 may comprise an aperture in the stent wall portion and may be in fluid communication with the tubular body 22 lumen 24.

At least a portion of the graft 50 may be disposed about at least a portion of the adjacent structural struts 26 which generally define the side branch opening 31. The graft 50 may comprise any suitable biocompatible material and is desirably a polymeric material. For example, polyethylene, polyurethane, PVC, polyamides, such as nylon 6, nylon 6,6, and the like, polyesters, such as PET and Dacron®, PEEK, SIBS, polypyrrole, polyethers and fluorinated polymers, such as tetrafluoroethylene (TFE), polytetrafluoroethylene (PTFE) and expanded polytetrafluoroethylene (ePTFE), and any suitable combinations thereof may be used.

Petals 52 may have any suitable size, shape and orientation. The petals 52 may be arranged about the side branch opening 31 in the stent 10 structure.

The graft 50 may cover any suitable portion of the stent 10. The graft 50 may generally extend outwardly from the region of the side branch opening 31 any suitable distance along the length of the stent 10 and any suitable distance about the circumference of the stent 10. In various embodiments, the graft 50 may extend about a portion of the stent 10 circumference or about the entire stent 10 circumference. In various embodiments, the graft 50 may extend along a portion of the stent 10 length or along the entire length of the stent 10.

FIG. 3 shows a cross-sectional view of a graft petal 52 and a portion of a stent. The stent member may comprise, for example, a portion of a serpentine band 12. The petal 52 may include an internal pocket 56, which may be formed between a first or outer material layer 54 and a second or inner material layer 58.

In some embodiments, for example as shown in FIG. 3, the graft 50 may comprise an inner material layer 54 and an outer material layer 58, and the material layers 54, 58 may be at least partially disposed about at least one structural strut 26. In some embodiments, the stent structural struts 26 (i.e. serpentine bands 12, etc.) may be sandwiched between the material layers 54, 58. Internal pockets 56 in the petals 52 may be formed by selectively connecting or bonding 57 the material layers 54, 58 where desired, for example about the perimeter of each petal 52. Layers 54, 58 may be bonded using any suitable method, such as melting under heat and pressure, chemical bonding or gluing, etc.

The internal pocket 56 of a petal 52 may be inflated, for example by injecting an inflation medium into the pocket 56. The inflatable pocket 56 may define an inflation lumen. The graft 50 may further comprise at least one inflation port 46 in fluid communication with the inflation pocket 56. An inflation port 46 may be located in any suitable portion of the graft 50, and in some embodiments may be located on any portion of a petal 52. An inflation port 46 may have any suitable orientation on the stent 10 and may be located on the inner side or the outer side of the graft 50. In some embodiments, an inflation port 46 may comprise a one-way valve arranged to allow fluid flow into the inflation pocket 56.

In some embodiments (not depicted in the drawings), the graft 50 may comprise a single layer of material, and the petals 52 and internal pockets 56 may be formed by adding a second layer of material in the petal 52 regions or any other suitable location. A single graft layer may be located on the inner side or the outer side of the stent structural members (i.e. serpentine bands 12, etc.), and a second layer added to form the pockets 56 may be located on the inner side or the outer side of the single graft layer.

Figure 4:
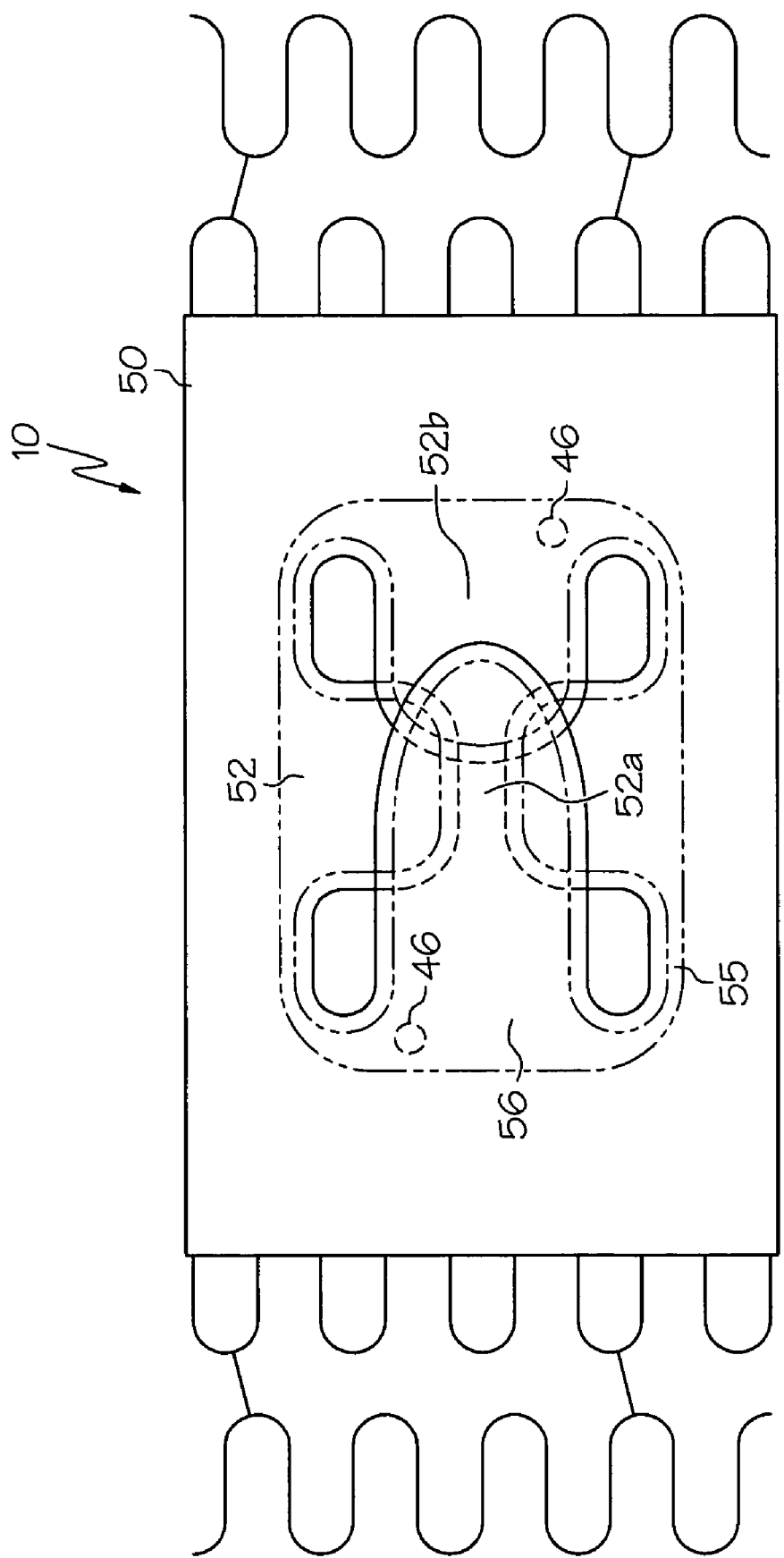
FIG. 4 shows an embodiment of an inventive stent in a delivery configuration.

FIG. 4 shows an embodiment of a stent 10 wherein the graft petals 52 are folded prior to outward deployment. In some embodiments, the petals 52 may be folded in a delivery configuration. In some embodiments, petals 52 may overlap one another in the delivery configuration and generally conform to the delivery shape of the cylindrical stent 10.

In some embodiments, the petals 52 may be asymmetrical in shape when compared to one another. For example, petal 52a is longer than petal 52b. This may be useful in some deployment locations where it is desirable for one side of the vessel bifurcation, such as the contralateral ostial wall, to receive support from a petal having a greater length or surface area than another side (i.e. the carina side).

An inflation pocket 56 may extend throughout each petal 52 and may extend between petals 52 via linking lumens 55. At least one inflation port 46 may be in fluid communication with the inflatable pocket(s) 56, and in some embodiments, a plurality of inflation ports 46 may be included at different locations of the graft 50. In some embodiments, multiple petals 52 may each have a separate inflation pocket 56 and a separate inflation port 46. Thus, a second petal 52 may include an independent second inflatable pocket (not shown) and an independent second inflation port (not shown). In some embodiments, a delivery system may be provided with a separate inflation lumen for each separately inflatable pocket.

The stent 10 may be delivered to a deployment site with the petals 52 in a folded delivery configuration. The stent 10 may be expanded to the expanded diameter. Upon injection of an inflation medium into the inflation pocket(s) 56, the petals 52 may unfold outwardly into a side branch vessel. The stent 10 may be manufactured with petals 52 capable of unfolding to any orientation or angle.

Stents 10 may be manufactured with petals 52 having a bias to assume a predetermined unfolded orientation. For example, the petals 52 may be biased to normally assume an orientation that is generally orthogonal to the longitudinal axis of the stent 10, as shown in FIG. 2. Petals 52 may be biased to any orientation by manufacturing the petal 52 in the predetermined orientation, such that the petal 52 may normally assume the biased shape absent any external loading. Petals 52 may then be folded for delivery, and may attempt to reassume the predetermined biased shape as the petal 52 is inflated.

Figure 5:
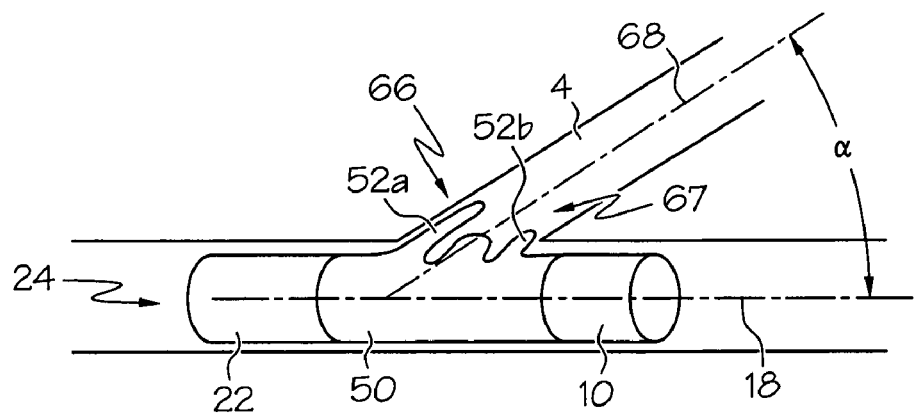
FIG. 5 shows an embodiment of an inventive stent in a deployment location.

Referring to FIG. 5, an embodiment of a stent 10 is shown having outwardly unfolded petals 52a, 52b extending into a side branch vessel 4. A longer petal 52a oriented to support a contralateral ostial wall may be arranged to normally unfold to an angle acute to the delivery configuration. A shorter petal 52b oriented to support the carina side of the bifurcation may be arranged to normally unfold to an angle obtuse to the delivery configuration.

In some embodiments, the plurality of outwardly deployed petals 52 may comprise a substantially tubular side branch body 66, which may define a side branch lumen 67 having a side branch longitudinal axis 68. The side branch lumen 67 may be in fluid communication with the lumen 24 of the tubular body 22. The side branch longitudinal axis 68 may form an angle α with the central longitudinal axis 18 of the tubular body 22. In some embodiments, the angle α may be 90°. In some embodiments, the angle α may be an oblique angle.

In some embodiments, a petal 52 may normally assume the delivery configuration and may unfold outwardly upon the injection of a pressurized medium into the inflation pocket 56. For example, the petal 52 may comprise an inner material 58 and an outer material 54 (see FIG. 3). The inner material 58 may be selected to have a higher elasticity than the outer material 54. Upon inflation, the petal 52 material may begin to stretch. The lesser elasticity of the outer material 54 may cause the petal to bend outwardly, similar to the operation of a bimetallic strip upon changes in temperature.

An inflated and unfolded petal 52 may retain its shape using any suitable method. In some embodiments, the inflation medium may have a flowable state and a hardened state, and may comprise a resin or fluid which may harden or solidify. For example, chemical mediums capable of hardening may be introduced in the form of an injectable polymeric material comprising a one part system, a two part system, self expanding systems, thermosets, thermoplastics, etc.

In some embodiments, a two-part chemical composition may harden upon the combination of the two parts. The inflatable pocket(s) 56 may be manufactured having an internal coating of one part of the two-part composition, and the second part may be injected, for example from outside the patient's body using a catheter or other suitable delivery device. In some embodiments, an inflatable pocket 56 may contain a predetermined amount of a first part of a two-part composition, for example in liquid form. A one-way valve may be used to prevent the first part from exiting the pocket 56. The second part may be delivered and injected into the pocket 56, passing through the one-way valve.

In some embodiments, an inflation medium may comprise a two-part activatable hardening material which may be injected into the pocket 56. A first part may be contained in a plurality of disruptable shells or microspheres. The disruptable microspheres may be mixed into the second part, and the entire composition may be delivered, for example in liquid form.

Upon agitation, the disruptable microspheres may release the first part, thereby mixing the two parts and allowing the composition to harden. Agitation may comprise any suitable agitation capable of disrupting the microspheres, such as the application of light including IR, visible or UV light which may be delivered through fiber optic cables. Agitation may further comprise mechanical vibrations which may be delivered by mechanical or electro-mechanical transducers. Agitation may further comprise the application of heat.

Polymeric systems may comprise vinyl or divinyl compounds in which an initiator is contained in the microspheres, epoxies containing microencapsulated amine component, or diisocyanates with encapsulated amine or hydroxyl terminated prepolymers. Amino groups can be so isolated from methylacetimidate, ethyl acetimidate, dimethylglutarimidate, dimethyl, adipidate, dimethyl sebaimidate, diisothionyl propionimidate, dimethyl oxydipropionimidatesuccinate bisesters, disuccinimidyl tartarate, dicyanatobenzene, dichlorodinitrobenzene, adipaldehyde, glutaraldehyde and the like.

In some embodiments, an inflation medium may comprise saline solution or any other suitable biocompatible fluid. A one-way valve may be used to allow the inflation medium to be delivered into the pocket 56 and retain the inflation medium within the pocket 56. Pressure of the inflation medium within the pocket 56 may retain the shape of the petals 52 and provide support to vessel walls.

Petals 52 may further be inflated according to any other suitable method, such as the examples disclosed in U.S. Pat. No. 5,871,537, the entire disclosure of which is hereby incorporated by reference in its entirety.

Figure 6:
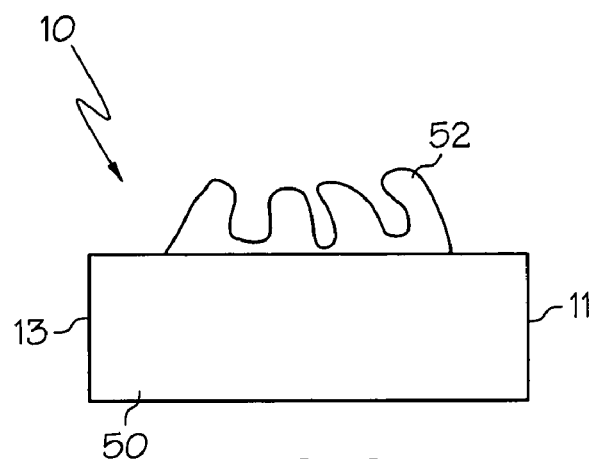
FIG. 6 shows an embodiment of an inventive stent.

FIG. 6 shows another embodiment of a stent 10 having inflatable petals 52. The petals 52 may have any suitable shape, orientation and distribution. The graft 50 may also extend to the ends 11, 13 of the stent 10.

Figure 7:
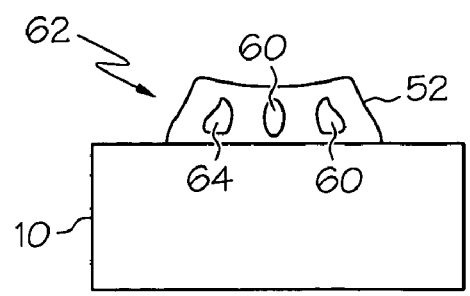
FIG. 7 shows an embodiment of an inventive stent.

FIG. 7 shows another embodiment of a stent 10 having inflatable petals 52. Adjacent petals 52 may be connected by linking portions 60 which may extend between the outer ends of the petals 52. In some embodiments wherein a petal 52 may comprise a first material 54 and a second material 58 (see FIG. 3), a linking portion 60 may comprise either material 54, 58 or may comprise both materials 54, 58. In some embodiments, a linking portion 60 may include an internal lumen or pocket which may be in fluid communication with the internal pockets 56 of the petals 52. A linking portion 60 having an internal lumen may comprise a linking lumen.

In some embodiments, a stent 10 may comprise an inflatable crown 62 which may include a plurality of apertures 64. An internal pocket 56 or a plurality of internal pockets 56 may extend throughout any portion of the crown 62. In some embodiments, a crown 62 may comprise a plurality of petals 52 and linking portions 60.

Figure 8:
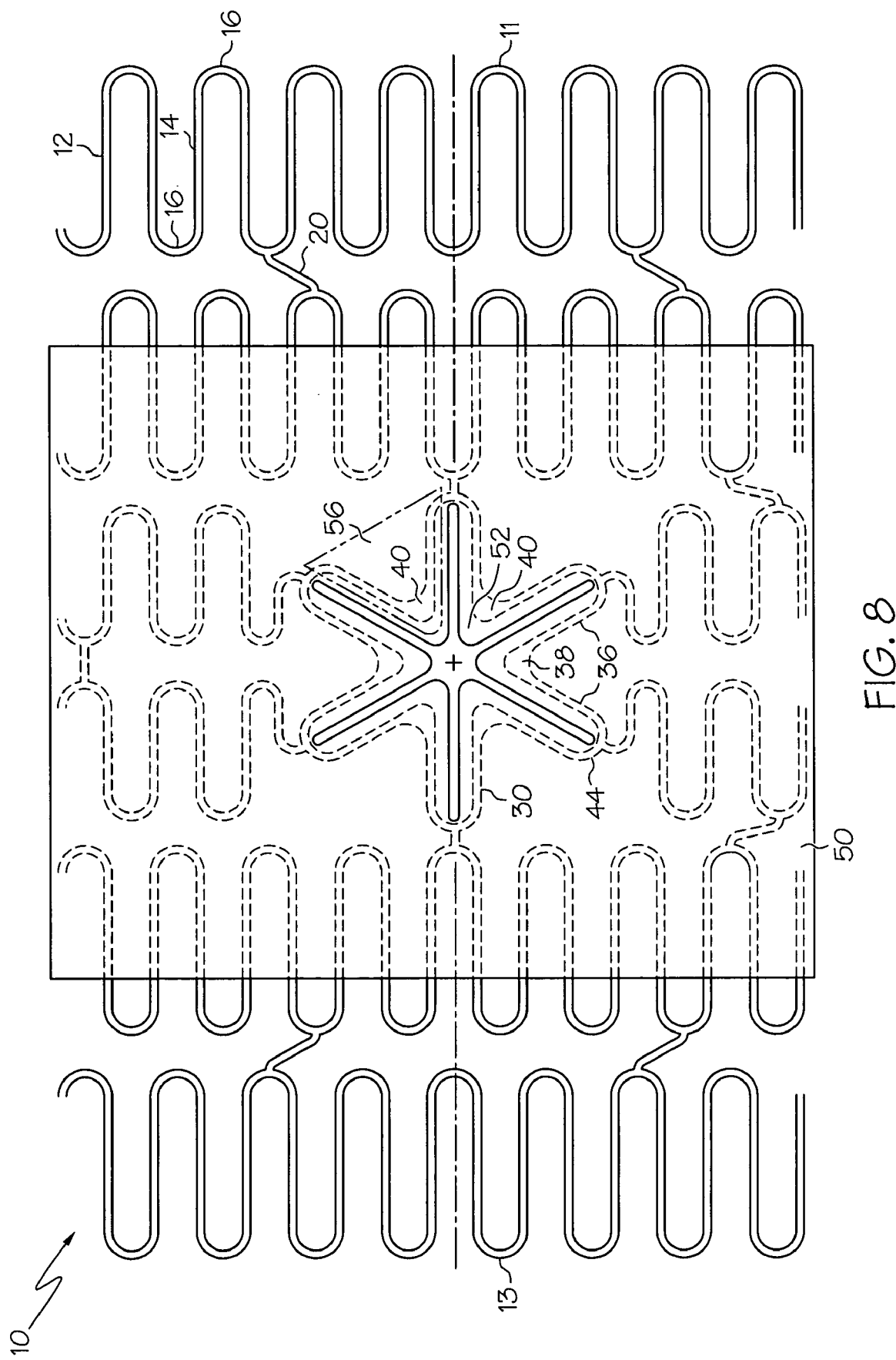
FIG. 8 shows an embodiment of an inventive stent having a structural side branch member.

Referring to FIG. 8, in some embodiments, structural members of a stent 10 may be included in and around the area of the petals 52. A structural side branch member 30 may comprise a continuous strut member, or in some embodiments a plurality of strut members, which may extend in a generally serpentine fashion about the center of the side branch opening. A side branch member 30 may have any suitable size, shape and configuration of struts.

In some embodiments, the side branch member 30 may define a plurality of structural side branch petals 40 which may have any suitable shape and may each be oriented in any suitable direction.

Each structural petal 40 may comprise a plurality of struts 36 and at least one turn 38. A strut 36 may be straight along its length, and may be oriented in any suitable direction. A turn 38 may be oriented in any suitable direction and in some embodiments may be oriented toward the center of the side branch opening. Structural petals 40 which are adjacent to one another about the side branch cell 30 may be connected to one another by a connecting portion 44.

Inflatable petals 52 may be provided in any configuration with respect to the structural petals 40. In some embodiments, the inflatable petals 52 and structural petals 40 may have a similar shape. In some embodiments, there can be a different number of structural petals 40 than inflatable petals 52. In some embodiments, structural petals 40 may be oriented about only a portion of the side branch opening, and inflatable petals 52 may be oriented about another portion, or about the entire side branch opening.

Inflatable petals 52 may be grafted to either side of side branch members 30, and in some embodiments the structural petals 40 may be sandwiched between inflatable petal 52 material layers. In some embodiments, an entire structural petal 40 or any portion thereof may be oriented within an inflatable pocket 56.

In some embodiments, the inflatable petals 52 and structural petals 40 may be outwardly deployed upon inflation of the inflatable petals 52. In some embodiments, the inflatable petals 52 and structural petals 40 may be outwardly deployed, for example by a separate inflation balloon, and the inflatable petals 52 may be subsequently inflated.

Other examples of stent structures which may be suitable for use with the invention are disclosed in U.S. Pat. Nos. 5,922,021; 6,123,721; 6,334,870; 6,478,816; 6,348,065; 6,325,826; and U.S. patent application Ser. Nos. 11/138,022; 11/138,196; and 11/138,202; the entire contents of which are hereby incorporated herein by reference in their entireties.

Stents 10 may be delivered to a deployment location and deployed using any suitable method. When an embodiment of a stent 10 includes structural petals 40 (see FIG. 8), it may be desirable to use a delivery catheter specifically designed to deploy the structural petals 40 outwardly, for example using an inflation balloon having a side branch deployment lobe. Some examples of stents having a side opening and methods of deploying such stents are disclosed in U.S. Pat. Nos. 5,596,020 and 6,835,203, the entire contents of which are hereby incorporated herein in their entireties.

Figure 9:
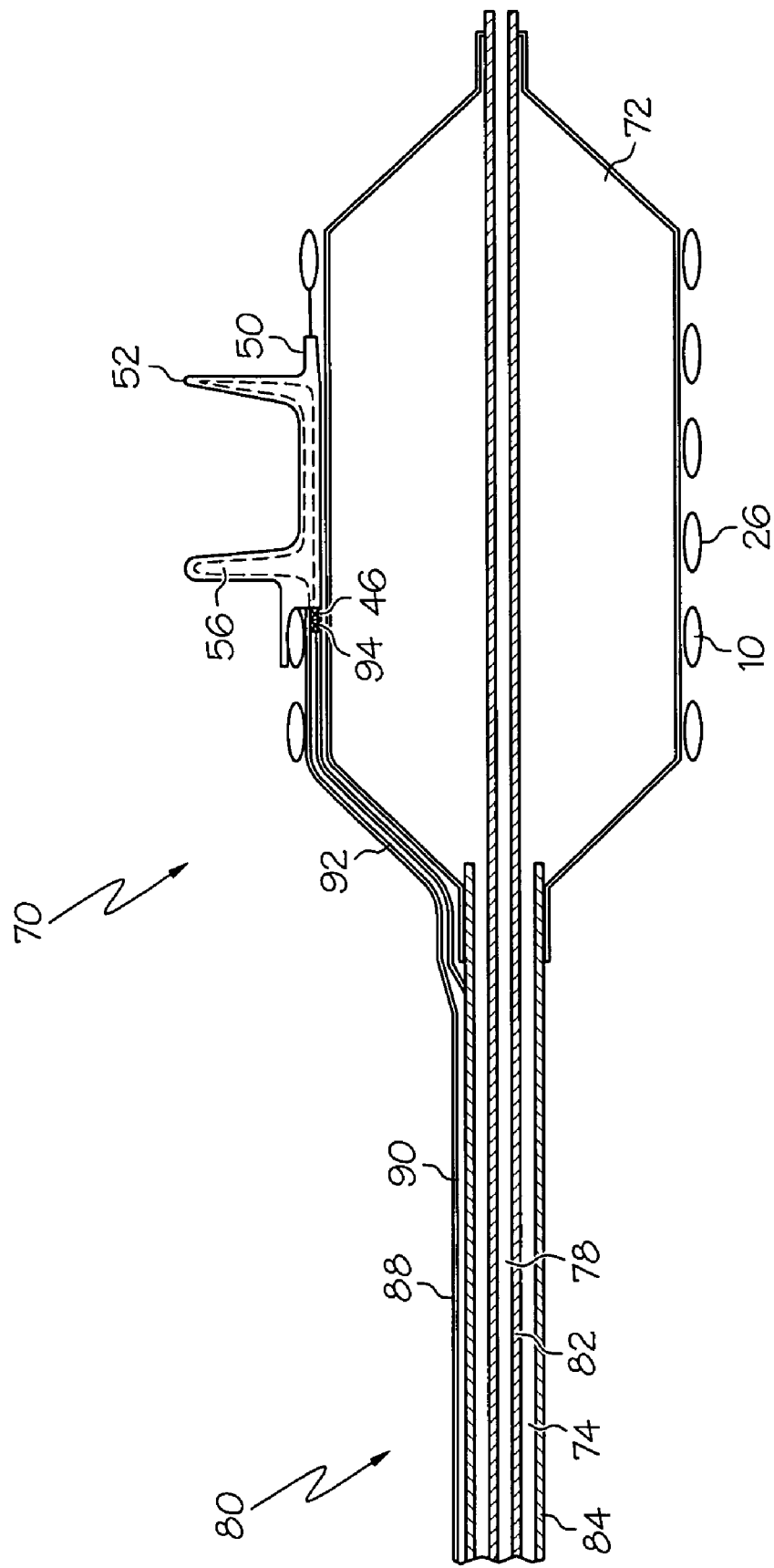
FIG. 9 shows an embodiment of a stent delivery system.

FIG. 9 shows an embodiment of a delivery system 70 suitable for deploying a stent 10 and the inflation petals 52. The delivery system 70 may comprise a catheter 80 and an inflation balloon 72. A stent 10 may be disposed about a portion of the balloon 72 prior to delivery and/or expansion. The catheter 80 may comprise any suitable structure and desirably includes an inflation lumen 74. As depicted, the catheter 80 comprises an inner shaft 82 and an outer shaft 84, and the inflation lumen 74 is oriented between the two shafts 82, 84. The inner shaft 82 may include a guidewire lumen 78. The inflation lumen 74 may be used to inflate the balloon 72 and expand the stent 10.

The delivery system 70 may further comprise an inflation member 88 which may define a catheter inflation lumen 90 which may be in fluid communication with the inflatable pocket(s) 56 of the inflatable petals 52 of the stent 10. The catheter inflation lumen 90 may be in fluid communication with an inflation port 46, which may be in fluid communication with the inflatable pocket(s) 56. A portion of the inflation lumen 90 may move outwardly with the stent 10 as the balloon 72 is inflated. In some embodiments, the inflation lumen 90 may include a flexible portion 92 which may allow the balloon 72 and stent 10 to expand while still maintaining fluid communication with the inflatable pocket(s) 56. A flexible portion 92 may extend from the inflation port 46 of the stent 10 to a location along the catheter 80 proximal to the inflation balloon 72. In some embodiments, a one-way valve 94 may be located between the inflation lumen 90 and the inflatable pocket(s) 56. An inflation port 46 may comprise a one-way valve 94.

In some embodiments, the delivery system 70 may be designed with a detachment point along the inflation lumen 90 to allow the inflation lumen 90 to be detached from the stent 10 after inflation of the inflation petals 52.

In some embodiments, the delivery system 70 may include multiple inflation lumens 90. When deploying embodiments of a stent 10 having multiple inflation pockets 56, multiple inflation lumens 90 allow for individual inflation of each inflation pocket 56.

In some embodiments of delivery systems to deliver stents to a bifurcation, a side branch guidewire may be provided, and in some cases a separate side branch catheter may be provided. Therefore, in some embodiments (not shown), an inflation lumen in fluid communication with the inflatable pockets 56 of a stent 10 may be included in a side branch catheter or side branch guidewire lumen.

While FIG. 8 shows an over-the-wire type catheter configuration, the invention is also directed to rapid-exchange type catheter configurations, for example where a guidewire may exit the guidewire lumen at some point along the length of the catheter shaft, fixed wire configurations or any other suitable type of catheter system.

In some embodiments, where the stent 10 may include a self-expanding structure, a delivery system may include a removable sheath, and the delivery system is not required to have an inflation balloon.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claims below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent expandable from an unexpanded state to an expanded state wherein in the expanded state the stent has a diameter that is greater than the diameter in the unexpanded state, the stent comprising:
   a substantially tubular body, the body defining a lumen and a longitudinal axis therethrough, the body comprising a plurality of structural struts, adjacent struts defining a side branch opening, the side branch opening being in fluid communication with the lumen;
   a graft, the graft disposed about at least a portion of the adjacent struts defining the side branch opening, the graft comprising an inflatable pocket, the inflatable pocket defining an inflation lumen and at least one inflation port in fluid communication therewith, the inflatable pocket comprising a petal, in the unexpanded state at least a portion of the petal positioned over the side branch opening, in the expanded state the petal extending outward from the tubular body to expose the side branch opening.

2. The stent of claim 1, wherein the petal is formed of a portion of the inflatable pocket comprising a first material layer and a second material layer.

3. The stent of claim 2, wherein the first material layer and the second material layer are at least partially disposed about at least one structural strut.

4. The stent of claim 1, wherein said petal comprises a first petal and said inflatable pocket comprises a first inflatable pocket, said stent further comprising a second inflatable pocket, the second inflatable pocket comprising a second petal.

5. The stent of claim 4, wherein the first petal overlaps the second petal in a stent radial direction when the petals are in the unexpanded state.

6. The stent of claim 4, wherein the first inflatable pocket and the second inflatable pocket are in fluid communication with one another.

7. The stent of claim 4, wherein the first petal and the second petal are connected by a linking member comprising a lumen in fluid communication with the first inflatable pocket and the second inflatable pocket.

8. The stent of claim 4, wherein the first inflatable pocket and the second inflatable pocket are separately inflatable.

9. The stent of claim 1, wherein in the expanded state a hardening inflation medium is positioned within the inflation lumen of the inflatable pocket.

10. The stent of claim 1, comprising a plurality of petals, in the expanded state the plurality of petals forming a substantially tubular side branch body, the side branch body defining a side branch lumen having a side branch longitudinal axis extending therethrough, the side branch lumen being in fluid communication with the lumen of the tubular body, the side branch longitudinal axis forming a non-zero angle with the axis of the tubular body.

11. The stent of claim 1, wherein in the unexpanded state a longitudinal axis of the petal is parallel to the longitudinal axis of the tubular body.

12. The stent of claim 11, wherein in the expanded state a longitudinal axis of the petal extends outward at an angle from the longitudinal axis of the tubular body, the angle being non-zero relative to the longitudinal axis of the tubular body.

13. The stent of claim 1, wherein the side branch opening has a perimeter, and wherein in the expanded state at least a portion of the petal extends outward from the tubular body and is engaged to at least a portion of the side branch perimeter.

14. The stent of claim 1, wherein the petal unfolds during expansion by rotating around a portion of a perimeter of the side branch opening.

15. A stent delivery system comprising:
a catheter shaft;
a substantially tubular stent;
a graft, the graft engaged to at least a portion of the tubular stent defining a side branch opening; the graft comprising a body portion and an outwardly deployable petal having an inflatable pocket, the petal attached to the graft body portion at an attached portion, the inflatable pocket defining an inflation lumen and an inflation port in fluid communication with the inflation lumen; and
an inflation member, the inflation member defining a catheter inflation lumen in fluid communication with the inflation port;
wherein the petal rotates around the attached portion as the petal is outwardly deployed.

16. The stent delivery system of claim 15, wherein the inflation port comprises a one-way valve between the inflation lumen and the inflatable pocket.

17. The stent delivery system of claim 15, wherein the inflation member comprises a flexible portion.

18. The stent delivery system of claim 15, wherein the catheter shaft further comprises an inflation balloon, the stent being disposed about a portion of the balloon prior to delivery.

19. The stent delivery system of claim 18, wherein the inflation member comprises a flexible portion extending from the inflation port to a location along the catheter shaft proximal to the inflation balloon.

20. A method of stenting a bifurcated vessel comprising:
providing a stent body having a graft engaged to at least a portion of the body; the graft comprising a body portion and an outwardly deployable petal having an inflatable pocket, the petal attached to the graft body portion at an attached portion;
orienting the stent at a deployment location; and
injecting an inflation medium into the inflatable pocket, thereby rotating the petal around the attached portion to deploy the petal outwardly from the stent body.

21. The method of claim 20, wherein the deployment location comprises a vessel bifurcation comprising a main vessel and a side branch vessel, wherein the stent is oriented within the main vessel and the petal is deployed outwardly into the side branch vessel.

22. The method of claim 20, wherein the inflation medium has a flowable state and a hardened state.

23. The method of claim 20, further comprising providing an expansion balloon and expanding the stent prior to injecting the inflation medium into the inflatable pocket.

24. The method of claim 23, wherein the stent further comprises an outwardly deployable structural petal comprising a structural strut member, and the method further comprises outwardly deploying the structural petal prior to injecting the inflation medium into the inflatable pocket.

* * * * *